(12) United States Patent
Staib et al.

(10) Patent No.: US 8,734,347 B2
(45) Date of Patent: May 27, 2014

(54) ANALYTICAL METHOD AND INVESTIGATION SYSTEM

(75) Inventors: Arnulf Staib, Heppenheim (DE); Hans-Martin Kloetzer, Mannheim (DE); Matthias Essenpreis, Weinheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1444 days.

(21) Appl. No.: 12/130,091

(22) Filed: May 30, 2008

(65) Prior Publication Data

US 2008/0262333 A1 Oct. 23, 2008

Related U.S. Application Data

(63) Continuation of application No. PCT/EP2006/011089, filed on Nov. 18, 2006.

(30) Foreign Application Priority Data

Dec. 3, 2005 (EP) .................................. 05026421

(51) Int. Cl.
*A61B 5/145* (2006.01)
*G06G 7/60* (2006.01)

(52) U.S. Cl.
USPC .............................. 600/365; 600/309; 703/11

(58) Field of Classification Search
None
See application file for complete search history.

(56) References Cited

U.S. PATENT DOCUMENTS

| 6,272,480 | B1 | 8/2001 | Tresp et al. | |
|---|---|---|---|---|
| 2004/0199409 | A1 | 10/2004 | Brown | |
| 2005/0004439 | A1 | 1/2005 | Shin et al. | |
| 2005/0038332 | A1* | 2/2005 | Saidara et al. | 600/347 |
| 2005/0203360 | A1* | 9/2005 | Brauker et al. | 600/345 |

FOREIGN PATENT DOCUMENTS

| DE | 4221848 C2 | 5/1994 |
|---|---|---|
| EP | 1102194 A2 | 5/2001 |
| WO | WO 0215777 A | 2/2002 |

OTHER PUBLICATIONS

Wikipedia Download on Fourier Transform Aug. 25, 2011.*
John J. Mastrototaro, "The MiniMed Continuous Glucose Monitoring System", Diabetes Technology & Therapeutics. Dec. 2000, 2(supplement 1): 13-18 (http://www.liebertonline.com/doi/pdfplus/10.1089/dia.2005.7.849).
T. Koschinsky, L. Heinemann, "Sensor for glucose monitoring; technical and clinical aspects", Diabetes/Metabolism Research and Reviews, vol. 17 Issue 2, 2001, pp. 113-123. XP002476174.
Boris P. Kovatchev, et al.,Quantifying Temporal Glucose Variability in Diabetes via Continuous Glucose; Monitoring: Mathematical Methods an Clinical Application, Diabetes Technology & Therapeutics. Dec. 2005, 7(6): 849-862 (http://www.liebertonline.com/doi/pdfplus/10.1089/dia.2005.7.849) (According to publishers Rightlink service, publication date is Jan. 12, 2005).
I. S. Kohane, I. J. Haimowitz, "Hypothesis-driven data abstraction with trend templates", Proc Annu Symp Comput Appl Med Care. 1993; 444-448. NLM8130513.
Velko et al., "Strategies for calibrating a subcutaneous glucose sensor", Biomed. Biochim. Acta 48 (1989) 957-964.
Sieg et al., "Implications for Noninvasive and Calibration-Free Glucose Monitoring", Biophysical Journal, 87 (2004) 3344-3350.
Derr et al., "Is HbA1c Affected by Glycemic Instability?", Diabetes Care, vol. 26, No. 10, Oct. 2003, 2728-2733.

\* cited by examiner

*Primary Examiner* — Karen Canella
(74) *Attorney, Agent, or Firm* — Faegre Baker Daniels LLP

(57) ABSTRACT

Metabolism diseases are evaluated by using a sensor to measure concentration of a medically significant analyte in a human or animal body fluid. The measurement data are correlated with the concentration of a medically significant analyte in body fluid over a time period of at least eight hours. An analytical facility analyzes time intervals within the time period to determine a stability parameter that characterizes the analyte concentration dynamics of change. The analytical facility further analyzes the stability parameters to determine disease-related particularities of metabolism.

14 Claims, 4 Drawing Sheets

ANALYTICAL METHOD AND INVESTIGATION SYSTEM

REFERENCE

This application is a continuation of PCT/EP2006/011089 filed Nov. 18, 2006 which is based on and claims priority to European Patent Application No. EP 05021983.1 filed Dec. 3, 2005, which are hereby incorporated by reference.

FIELD

The disclosure relates to a method for analyzing a series of measuring data that are correlated with the concentration of a medically significant analyte in a human or animal body fluid. The disclosure also relates to a system for investigating the metabolism of a human or animal with regard to a medically significant analyte. Important body fluids in this context are, e.g., blood and interstitial fluid as well as other fluids to which a sensor that is implanted in tissue can be exposed.

BACKGROUND

Glucose is one of the most important medically significant analytes in human body fluids. For this reason, reference is made to glucose in the disclosure as an example for a medically significant analyte in a human or animal body fluid without limiting the general scope of the invention.

Continuous monitoring of the blood glucose concentration, during which measuring values are obtained, for example, every few minutes, are known according to the prior art under the term, "continuous monitoring," for example from U.S. Pat. No. 6,272,480 or European Pat. No. EP 1102194A2. The aim of these applications is to administer the insulin doses required for the treatment of diabetes at optimal points, in time in optimal quantities in order to maintain the blood sugar level of a diabetic within narrow limits, as is the case in a healthy person.

The blood glucose concentration of a patient is of extreme medical significance. According to the results of studies, extremely serious long-term consequences of diabetes mellitus (for example loss of eyesight due to retinopathy) can be prevented by careful monitoring of the blood sugar level and by keeping the blood sugar level within narrow limits.

Systems for the investigation and monitoring of glucose metabolism have a sensor module that facilitates continuous or quasi-continuous measurement of the analyte concentration. Suitable sensors can, for example, be implanted directly into subcutaneous fatty tissue or blood vessels. It is also feasible to implant catheters by means of which an exchange between a dialysate and the surrounding body fluid is utilized for collecting analytes. The dialysate can be transported via microfluidics to a sensor that is situated outside the body. In principle, it is also feasible to measure analyte concentrations by means of a non-invasive sensor that is, for example, glued to the skin.

Known systems for the monitoring of the glucose concentration aim to counteract a dangerous increase of the blood glucose concentrations in due time by administering a dose of insulin. For this purpose, it is often desired to be able to predict future blood glucose concentrations over a period of time of approximately half an hour on the basis of previously determined measuring values such that a dangerous increase of the glucose concentration can be prevented by timely administration of a dose of insulin, e.g., U.S. Pat. No. 6,272, 480.

To allow an analyte concentration to be determined from a raw or measuring signal, for example an electrical current, of a sensor, the sensor that is employed for this purpose must be calibrated in a resource-consuming fashion. An underlying prerequisite for successful calibration is that raw signals that are output by the sensor show a sufficient correlation with reference values of the analyte concentration that are determined on body fluid samples obtained from the body. In particular in the case of implanted sensors, the measuring sensitivities can change markedly over time such that renewed in-vivo calibration may be required in regular intervals. Problems of the calibration of implantable sensors and approaches to solutions thereof are summarized in the publication, G. Velho et al., "Strategies for calibrating a subcutaneous glucose sensor", Biomed. Biochim. Acta, pp. 957-964, vol. 48 (1989).

In principle, calibration problems might be prevented by concomitantly measuring an internal standard. This approach is described in the publication, A. Sieg et al, "Electroosmosis in Transdermal Iontophoresis: Implications for Noninvasive and Calibration-Free Glucose Monitoring," Biophysical Journal, pp. 3344-3350, vol. 87 (2004).

SUMMARY

It is an object of embodiments of the invention to devise a way in which disease-related particularities of the metabolism of a human or animal can be determined by analyzing a series of measuring data that is associated with a reduced calibration effort or no calibration.

This object is met by a method for analyzing a series of measuring data g that are correlated with the concentration of a medically significant analyte in a human or animal body fluid for time points $t_1$ to $t_n$ that are distributed over a period of time of at least 8 hours, such as least 24 hours, whereby multiple time intervals each extending over at least 1 hour are selected from the period of time, a stability parameter characterizing the dynamics of the change of the analyte concentration in said time interval is determined for each of the time intervals by analyzing measuring data g that are from said time interval, and the stability parameters are analyzed in order to determine disease-related particularities of metabolism.

The series can contain measuring data at a density of at least three data points per hour, and some embodiment can have at least 6 data points per hour or at least 10 data points per hour.

Known methods aim to determine the analyte concentration as precisely as possible and therefore necessitate resource-consuming calibration of the sensors used. In a method according to embodiments of the invention, though, there is no need to determine the absolute concentration values, because disease-related particularities can frequently be recognized already by means of the dynamics of the change of analyte concentrations in the body fluid. For investigation of the dynamics of analyte concentrations, it is sufficient to determine measuring data that are correlated with the analyte concentration such that absolute concentration values are not required and resource-consuming calibrations of the sensor used are not needed either.

Embodiments of the invention also relate to the system for investigation of the metabolism of a human or animal with regard to a medically significant analyte, comprising an analytical facility which, in operation, is adapted to perform the following steps.

Analyzing a series of measuring data g that are correlated with the concentration of a medically significant analyte in a human or animal body fluid for time points $t_1$ to $t_n$ that are distributed over a period of time of at least 8 hours, preferably at least 24 hours, by selecting from the period of time multiple time intervals, which each extend over at least one hour.

A stability parameter characterizing the dynamics of the change of the analyte concentration in said time intervals is determined for each of the time intervals by analyzing measuring data that are from said time interval.

The stability parameters are analyzed in order to determine disease-related particularities of metabolism.

The system further comprises a sensor for determining measuring data that correlated with the concentration of a medically significant analyte in a human or animal body fluid.

The selected time intervals can be right next to each other, however it is also feasible to select overlapping time intervals or time intervals that are separate from each other. In this context, the analysis of individual time intervals can be initiated even before the complete series of measuring data is available. i.e., before the entire period of time from which the time intervals are selected has elapsed.

BRIEF DESCRIPTION OF THE DRAWINGS

Further details and advantages of embodiment of the invention are illustrated on the basis of an exemplary embodiment and by making reference to the appended drawings. The particularities shown therein can be used alone or in combination in order to create further embodiments of the invention. In the figures.

DETAILED DESCRIPTION

Figure 1:
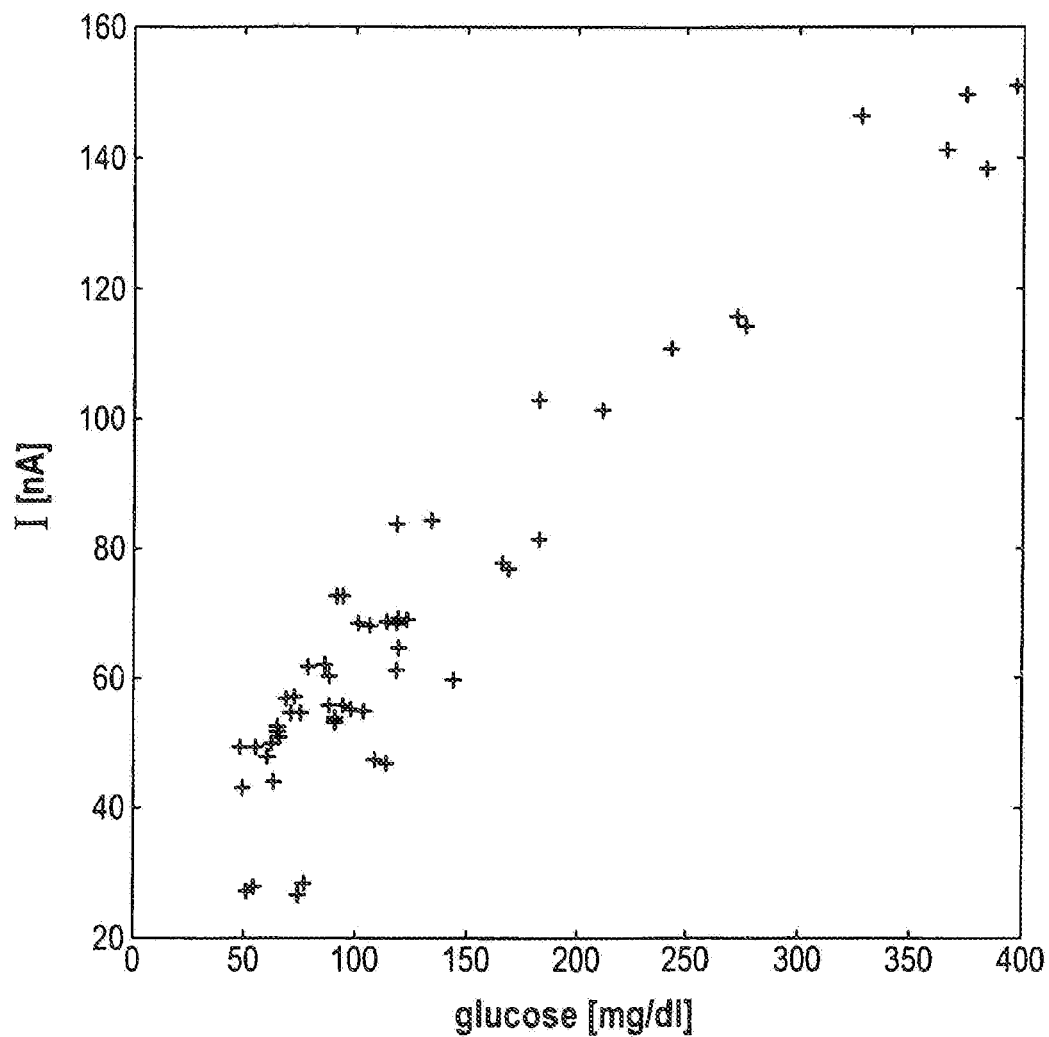
FIG. 1 shows an example of raw data of an implanted sensor, in nanoamperes, plotted over the blood glucose concentration, in mg/dl.

FIG. 1 shows raw data, in nanoampere, that were measured using a sensor implanted in the subcutaneous fatty tissue of a subject, plotted over the blood glucose concentration, in mg/dl. The glucose content was determined on capillary blood using a conventional blood sugar, measuring device.

The raw data shown in FIG. 1 could be used in conjunction with the concomitantly measured concentration values of the abscissa to calibrate the sensor. However, this is not required according to the scope of the invention. In the method described in the following, it is sufficient to have available measuring values that are correlated with blood glucose concentration.

In the example shown in FIG. 1, the raw data, that were determined with an implanted sensor show proportionality to the analyte concentration, disregarding noise and interfering, signal fractions. It is not rare for sensors to have non-linear characteristic curves such that the raw data are transformed in a non-linear fashion according to a characteristic curve in order to generate measuring values that show improved correlation with the analyte concentration, in particular are proportional to the analyte concentration, disregarding noise and interfering signals.

There may, for example, be the following non-linear relationship between the measured current I of a sensor and the analyte concentration c:

$$I = I_0 + I_g(1 - \exp(-c/c_r))$$

In this characteristic curve, $I_0$ is a zero or background current that is present when the analyte concentration c=0; $I_g$ is a limit current that is added to the zero current $I_0$, theoretically, at infinitely large analyte concentration c; and $c_r$ is a reference concentration that characterizes the sensitivity of the sensor. The parameters, $I_0$, $I_g$, and $c_r$, can be determined ex-vivo during manufacture for a sensor type or a production batch with little expense of resources.

Upon implantation of a sensor of this type, in particular the parameters, $C_r$ and $I_g$, change such that absolute concentration values cannot be determined using a characteristic curve that was determined at the factory. However, this is not required for the method described in the following. Rather, it is sufficient that measuring values can be determined from raw data by means of a characteristic curve of this type, whereby said measuring values are proportional to the analyte concentration, disregarding noise and interference signal fractions, i.e. are high correlated with the analyte concentration.

Depending on the type and quality of the raw data determined, these data can be used directly as measuring values for the method according to embodiments of the invention or the measuring values must first be calculated from raw data, for example by means of a statistical analysis or a non-linear transformation according to the characteristic curve of the sensor that is used.

In the example shown in FIG. 1, the coefficient of the correlation between the raw data and the glucose concentration is R=0.95 such that these can be used directly as measuring values. Working with high-noise raw data showing only relatively poor correlation with the glucose concentration, it is advisable to use statistical analysis or suitable filter algorithms to generate measuring values that show a markedly improved correlation with the analyte concentration as compared to the underlying raw data.

In this context, for the purposes of the disclosure, the term correlation shall also be understood to mean an anti-correlation since multiplication of the measuring values by a factor of −1 would not change the essential relationships between the measuring values and the underlying analyte concentrations. The method described in the following can be used to analyze measuring values whose correlation coefficient with regard to the glucose concentration has a numerical value of at least 0.5, such as at least 0.7, or such as at least 0.9. However, in principle, the method is also applicable to measuring data with poorer correlation coefficients, whereby the significance of the results obtained in cases of this type is correspondingly lower.

It is important for understanding the method described in the following that the correlation situation shown in FIG. 1, and in particular the numerical value of the correlation coefficient, does not change upon application of a linear transformation $f$. A linear transformation can generally be expressed as $f = ax + b$. This means that a measuring value x is multiplied by a constant factor a in a linear transformation and a constant factor b is added to the result thereof. Geometrically, this corresponds to a stretching or compressing the ordinate axis and a shift of the measuring values in the direction of the ordinate axis in the example shown in FIG. 1.

Figure 2:
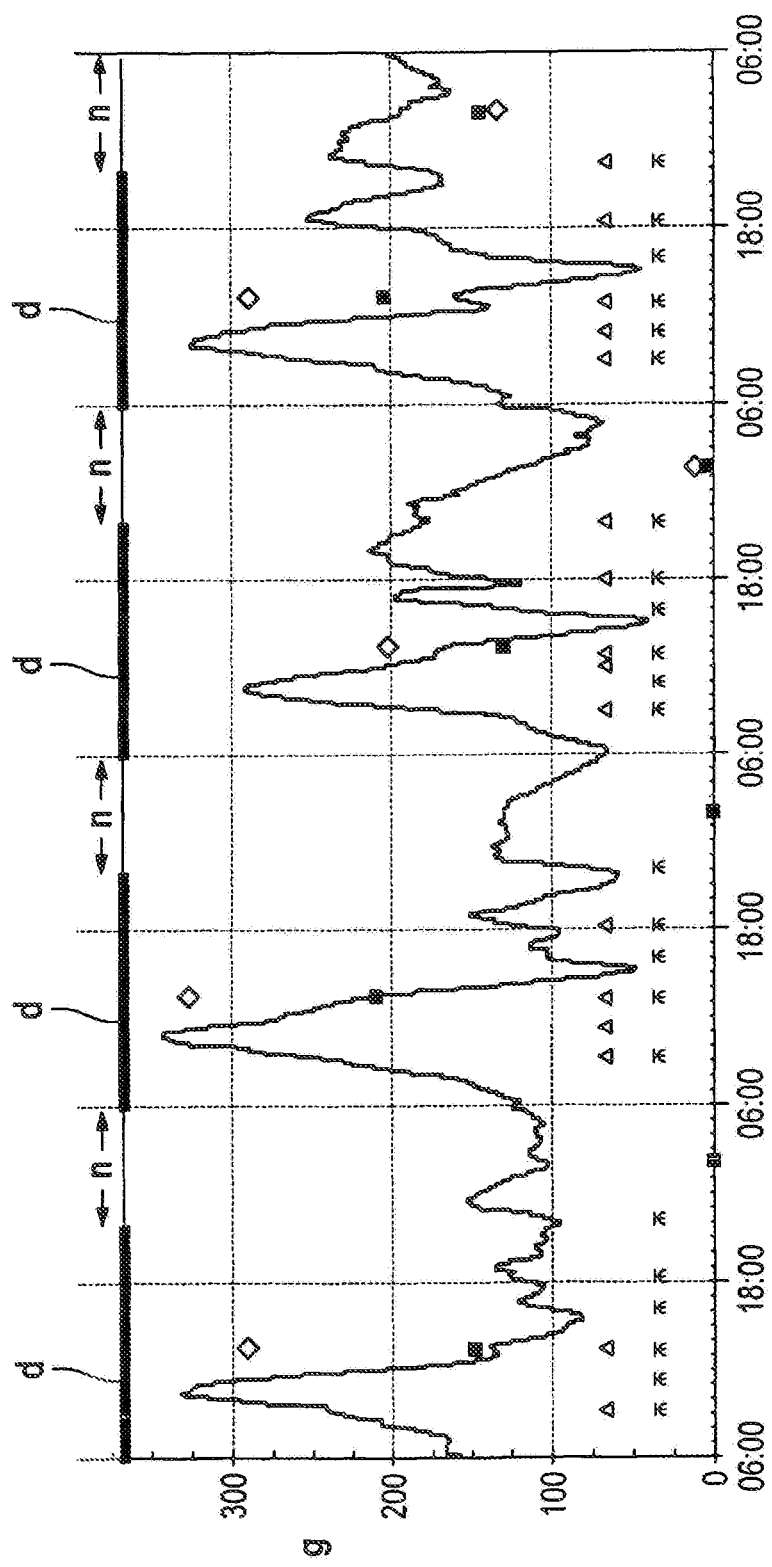
FIG. 2 shows an example of the profile of measuring values of an implanted glucose sensor over a time period of four days.

FIG. 2 shows a series of quasi-continuous measuring data g in arbitrary units plotted over the time t over a period of 4 days. In this context, times of day belonging to the measuring data are plotted on the abscissa. The measuring data shown in FIG. 2 are based on linearly-transformed measuring data, such as are shown in FIG. 1, which were smoothed retrospectively using a median filter and an adaptive recursive filter.

Time intervals d, n, corresponding to day and night times in the exemplary embodiment shown and therefore reflecting the profile of the analyte concentration for waking times and times of night rest, were selected from the time period of four days shown in FIG. 2. In general, it is useful to select time intervals that are correlated with characteristic phases of the investigated metabolism, such as is the case in selecting pre- and post-prandial phases or day and night times, from the period of time over which the time points $t_1$ to $t_a$, which the measuring data $g(t_1)$ to $g(t_n)$ of the series apply, are distributed.

For each of the selected time intervals, a stability parameter characterizing the time course of the change of analyte concentration in the period of time is determined by analyzing measuring data g that are from the corresponding time interval. This stability parameter is analyzed in order to determine disease-related particularities of metabolism. By this means, an early diabetic disease can be recognized of, in the case of an insulin-dependent diabetic, a recommendation concerning the adjustment of insulin doses can be assigned in case a disease-related particularity of glucose metabolism is determined.

For calculation of the stability parameter, firstly, measuring data g are calculated from measuring values, such as the ones shown in FIG. 1, whereby a linear transformation $f$ is performed as a calculation step. It is preferable to perform, in addition, further calculation steps, in which the measuring values are processed and smoothed with suitable filter algorithms and statistical methods before or after performing the linear transformation $f$.

If the measuring, sensitivity of the sensor used is sufficiently constant over time, the same transformation can be used for multiple intervals. However, the measuring sensitivity and/or the background signal often changes in the case of implanted sensors such that it is preferable to define a transformation f individually for different intervals.

In this context, the linear transformation $f$ is selected for the individual time intervals such that the mean of the measuring data g of the corresponding time interval corresponds to a predefined value. Preferably, this predefined value is 0, but, in principle, any other constant can be selected as well. For example, the linear transformation $f$ can be selected such that interval limits are predefined and the smallest measuring data point is assigned to the lower interval limit, for example to the value 0, and the largest measuring data point is assigned to the upper interval limit, for example to the value 1.

Since, a linear transformation $f$ contains two selectable parameters according to the equation $f=ax+b$, namely the slope a and an additive constant b, the linear transformations $f$ are not yet determined unambiguously by predefining a mean of measuring data or interval limits. Moreover, the linear transformations $f$ each are selected such that the standard deviation of the measuring data g of the corresponding time interval corresponds to a predetermined value, for example 1.

In order to calculate the stability parameter S for the corresponding interval, the first derivative over time g' of the measuring data g is formed in a calculation step. Since measuring data are usually available in the form of discrete measuring, points, i.e. quasi-continuous in the best case, the first derivative over time g' is formed by numerical means, for example using a polynomial filter. The standard deviation of the values of the derivative over time g' of the corresponding interval is calculated in a further calculation step.

The standard deviation thus determined characterizes the dynamics of the change of analyte concentration in the examined time interval and can therefore be used directly as stability parameter. However, it can also be useful to use a function of the standard deviation, for example the standard deviation squared, as stability parameter.

The glucose metabolism of a healthy subject is characterized by inherent regulatory mechanisms rapidly counteracting any increase of the glucose concentration that is due to food intake such that the standard deviation of the values of the derivative over time g' is relatively large. After a rapid increase follows a rapid decrease such that the first derivative overtime g' takes on both high positive as well as high and negative values in a time interval.

In a diabetic, the inherent regulatory mechanisms are disturbed such that elevated glucose concentration values are reduced only relatively slowly. For this reason, high positive and small negative values of the first derivative over time g' are typical to occur in a diabetic. Consequently, a diabetic disease leads to the standard deviation of the values of the derivative over time g' being markedly smaller than in a healthy reference person.

Analysis of the stability parameter, for example by assigning it to predetermined parameter ranges, allows a disease-related particularity of metabolism to be determined, in particular a diabetic disease and/or the stage of a diabetic disease to be diagnosed. Analysis of the stability parameters allows a recommendation for setting of the dosing of insulin doses of an insulin-dependent diabetic to be assigned to the disease-related particularities of glucose metabolism thus determined.

Optimal dosing of insulin doses is associated with substantial problems according to the prior art. In practical application, the selected insulin dosages are based to a substantial part on the experience of the attending physician or of the patient. Typically, a physician sets up for a diabetic a dosing plan that predetermines, on the one hand, the quantity and frequency of insulin doses for covering a basic insulin need and also includes instructions detailing how to dose additional insulin doses in response to elevated glucose concentration measuring values and intake of meals. In this context, insulin doses for covering the basic insulin need are termed basal rate and additional insulin doses related to intake of meals are termed bolus. The general dosing instructions according to which a diabetic determines the dosage of the insulin doses to be administered is termed dose setting or adjustment.

Aside from the dose setting of insulin-dependent diabetics, the so-called diabetes management comprises a number of other essential items aiming to reduce the probability of metabolic imbalances (E. Standl et al, "Grundlagen des Diabetes-Managements," Diabetologic in Klinik und Praxis, Ed. H. Mehnert et al., Thieme Verlag, Stuttgart, pp 132 (2003). The most important component of diabetes management aside from dose titration is self-control of metabolism, primarily of the glucose level, but possibly also of cumulative parameters such as ketone body concentrations, IIbA1c or glycolized scrum proteins. Diabetes management typically also includes non-medication therapeutic measures (e.g. nutritional plan, physical exercise) and, in particular in type 2 diabetics, medication-based measures, such as oral antidiabetics. Another important component of diabetes management is the monitoring of the total risk profile, specifically with regard to diabetes-related late damage, whereby investigations of renal function, lipid profile, and blood pressure can be taken into account in addition. In this context, a central component of a diabetes management system is the long-term application of a documentation system in which the data on self-control of metabolism and dose titration mentioned above, but also data on nutrition and other relevant events are stored. The methods described can make an important contribution to a diabetes management system, since analysis of the stability parameters allows important data concerning disease-related particularities of metabolism to be determined.

The method described above can be used to determine recommendations concerning the adjustment of insulin doses or related to diabetes management in general, for example related to non-medication therapeutic measures, by means of analyzing the stability parameters even without knowing the absolute glucose concentration values. If, for example, a strong increase of glucose concentration is experienced in a time interval after intake of a meal and is reduced only slowly or incompletely, the standard deviation of the values of the derivative over time g' of the measuring data g is smaller than would be the case upon rapid and complete restoration of the glucose concentrations to the physiological equilibrium concentration. In this case, it would be indicated to increase the bolus of insulin doses. Alternatively, it may be recommended as part of diabetes management, for example, to reduce the intake of bread units during intake of a meal or to counteract the increase of the glucose concentration after intake of a meal by means of physical exercise. By analyzing the stability parameters of time intervals, in which no intake of meals occurred, it can be checked whether the titrated basal rate corresponds to the needs of the patient.

The use of a computer is recommended in order to be able to perform the described analysis of the measuring data g and to generate these from measuring values in accordance with FIG. 1. For this reason, the method described is preferably implemented in the form of a computer program product that can be loaded directly into the memory of a digital computer and comprises software sections that can be used to perform the steps of the method described above when the program runs on a computer.

In order to be able to determine disease-related particularities of the investigated metabolism as reliably as possible, multiple stability parameters are analyzed. In this context, it is preferable to determine from the stability parameters of various time intervals a stability vector whose components characterize the time course of the change of analyte concentration in the corresponding time interval for one time interval each. In the simplest case, the components of the stability vector are the stability parameters that were determined for the corresponding intervals.

Figure 3:
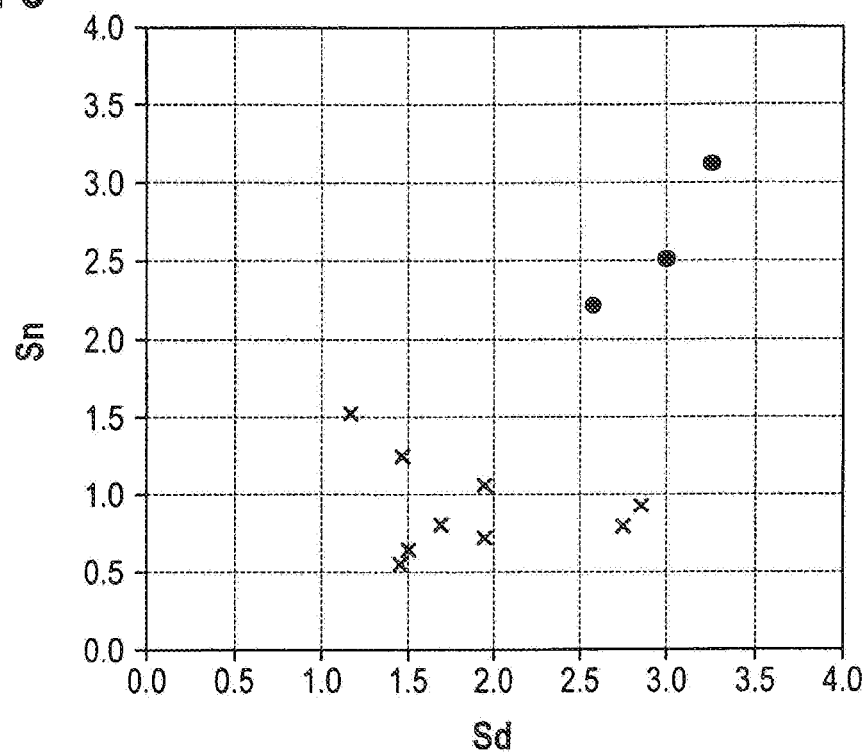
FIG. 3 shows stability parameters for various subjects that have been determined by means of the method according to embodiments of the invention.

Examples of a stability vector of this type are plotted for various subjects in FIG. 3. The stability vector shown in FIG. 3 has two components, namely a stability parameter Sd for waking times of the subjects (06.00 h to 22.00 h) and a stability parameter Sn for times of night rest (22.00 h to 06.00 h). The corresponding time intervals d, n are indicated in FIG. 2. The abscissa in FIG. 3 indicates the value of the stability parameter Sd for waking times and the ordinate indicates the value of the stability parameter Sn for times of night rest in arbitrary units. Stability vectors of healthy subjects are shown as circles (●), stability vectors of diabetics are shown by crosses (X) in FIG. 3.

It is evident from FIG. 3 that the values of the stability parameters of diabetics are clearly lower as compared to healthy subjects, particularly at night. This is, in part, because the (damaged) inherent regulatory mechanisms of insulin-dependent diabetics are supported by external insulin doses during the day. Accordingly, optimal setting of the insulin doses allows the stability parameter Sd for waking, times to attain values that are comparable to values of healthy subjects. At night, though, there is no comparable support for the inherent regulatory mechanisms by external insulin doses such that the concentration values are more poorly controlled due to the disease and therefore the stability parameter Sn is observed to take on smaller values.

An alternative stability parameter for an application of this type can be obtained by means of a frequency analysis of the first or second derivative over time g' org'' of the measuring data g. For a sufficiently long time window, the derivatives over time are basically stationary, i.e. they have no significant positive or negative trend-over said window. Good stability of metabolic control is then indicated by an accumulation of fluctuations in the time course of g' or g''. A Fourier transformation of the derivative over time g' org'', specifically the calculation of a power spectrum, facilitates analysis of these fluctuations.

Poor stability of control leads to low frequencies occurring to an increased extent in the power spectrum. For this reason, for example, the ratio of the spectral intensity of high frequencies to the spectral intensity of low frequencies in the power spectrum of the derivative over time g' of the measuring data g can be a stability parameter. In analogous fashion, the ratio of the spectral intensity of high frequencies to the spectral intensity of low frequencies in the power spectrum of the second derivative over time g'' of the measuring data g can be used as a stability parameter.

In principle, programmable insulin pumps can be used to improve the stability of the control of glucose concentration also in night phases. Analysis of the stability parameters determined using the method described allows the pump rate of an insulin pump of this type to be checked, and adapted if needed, for example by comparing stability parameters that have been determined to predetermined parameter ranges and increasing or decreasing the pump rate for the corresponding time in the day upon an upward or downward deviation, respectively.

In this context, it must be noted that most humans have a regular daily routine and therefore the time course of the change of analyte concentration is also dominated by a 24-hour rhythm. Insights that were obtained, for example, for times of night rest from observations over a number of days can therefore be applied to future periods of night rest. For this reason, stability parameters of comparable time intervals can be subjected to statistical analysis, for example by calculating the mean, in order to improve the reliability of the results obtained.

In the simplest case, time intervals that are limited by identical times of day are always comparable. However, the start of an interval can also be defined by a relevant event in the day, in particular the intake of a meal. This procedure is recommended in particular with regard to people having a rather non-regular daily routine.

Figure 4:
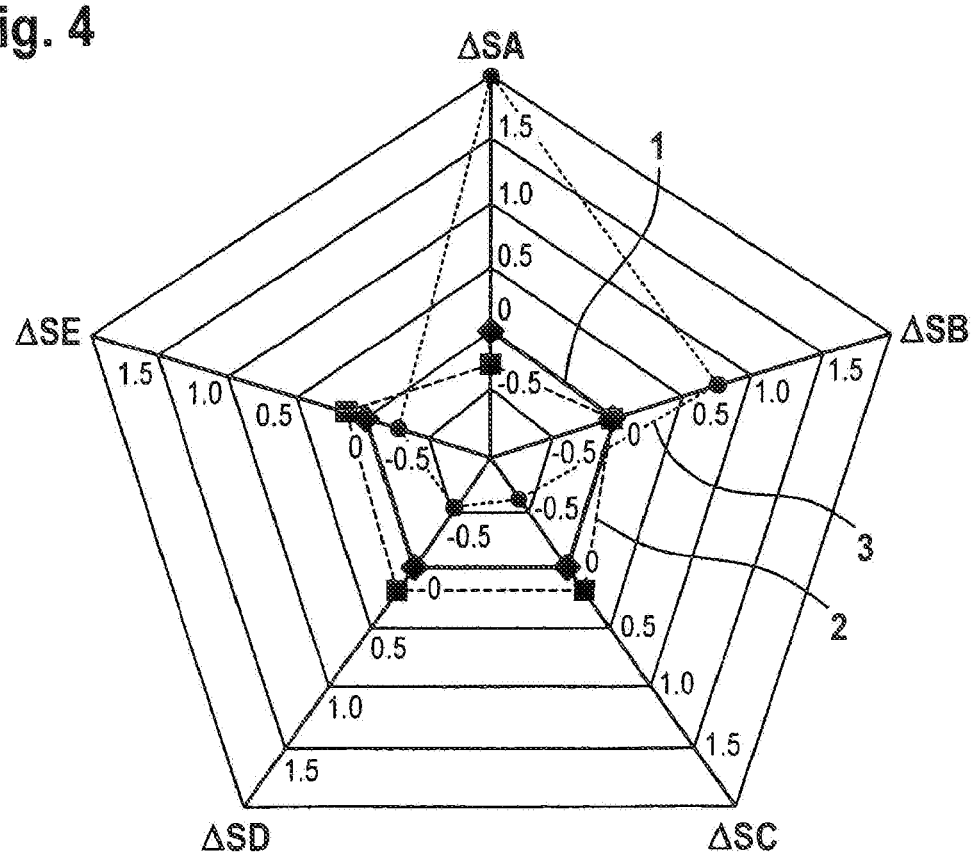
FIG. 4 shows a comparison of the stability parameters of a healthy subject and stability parameters of insulin-dependent diabetics for five consecutive time, intervals.

In the example shown in FIG. 4, the night phases n of the measuring data g shown in FIG. 2 each were subdivided into five consecutive intervals A, B, C, D, E with a duration of 1.6 hours each, and for each corresponding interval the mean was calculated from the stability parameters that were determined for the individual intervals of the different nights. By this means, a stability vector comprising five components SA, SB, SC, SD, SE, was calculated, whereby each of the five components is a mean of four stability parameters that were determined for the corresponding interval in the four nights of FIG. 2.

FIG. 4 shows for three subjects the deviation, ΔSA, ΔSB, ΔSC, ΔSD, ΔSE, of the components, SA, SB, SC, SD, and SE, of the stability vector thus determined from an ideal value (2.5 in the arbitrary units of FIG. 3) in a pentagram. From the center of the pentagram and through its corners extends an axis each that indicates the value of the deviation ΔS of the stability parameter S from the ideal value in the corresponding time interval.

It is self-evident that this method can also be applied to an entire day or a different period of time or/and a different subdivision. In this case, a presentation in accordance with FIG. 4 results in a n-corner diagram, whereby each corner of the diagram has one component of an n-component stability vector assigned to it. In a healthy subject, the deviation ΔS of the stability parameter S from the ideal value is defined to be zero.

Line 1 in FIG. 4 indicates, as a reference, the ideal profile of the deviations ΔS=0 of the stability parameters of a healthy subject. For comparison, the results of two diabetics are shown by dashed lines 2, 3. Comparing the profile of lines 2, 3 of insulin-dependent diabetics to line 1 of the healthy subject, it is evident that line 2 shows relatively little deviation from the ideal profile of a healthy subject which leads to the conclusion that only minor disease-related particularities of metabolism are manifest in the corresponding subject. Line 3 indicating the deviation ΔS of the stability parameters for the other diabetic shows a marked deviation from the ideal profile, though. This indicates that the setting of insulin doses should be adapted in the corresponding patient.

In a presentation in accordance with FIG. 4, the area between lines 2, 3 of a subject to be investigated and the reference line can be analyzed to determine the quality of glycemic self-control and therefore the quality of the setting of insulin dosages also.

Figure 5:
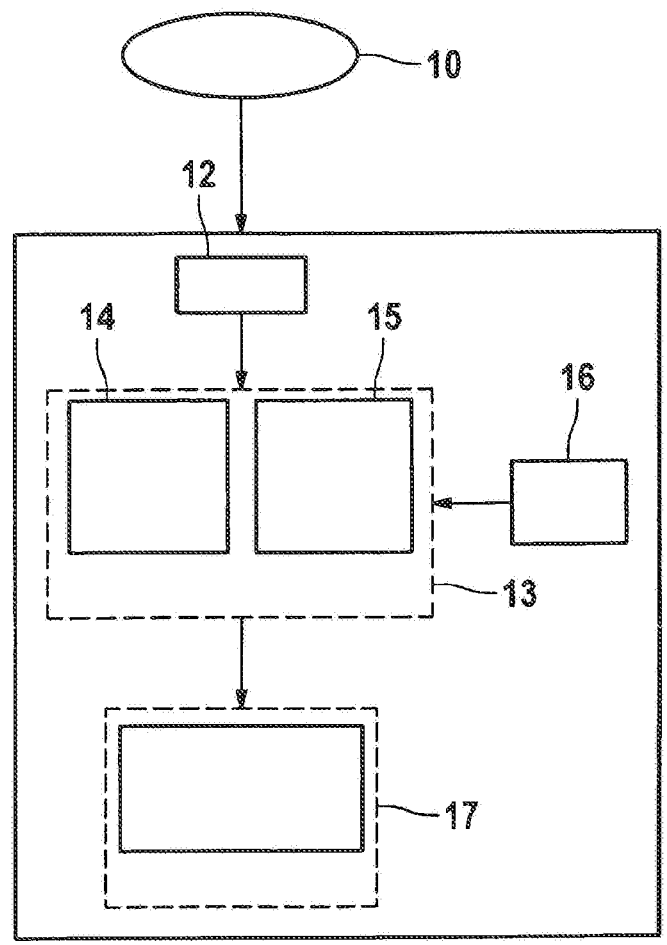
FIG. 5 shows a schematic view of a system according to the invention.

FIG. 5 shows the essential components of a system that can be used to investigate the metabolism of a human or animal according to the method described above. A measuring unit uses a sensor 10 to measure $t_n$ measuring values at consecutive time points. The measuring values are then transmitted—by wireless transmission in the case shown—to a receiver 12 that passes the measuring values on to an analytical facility 13 that contains a microprocessor 14 and a data memory 15. Results are being output by means of an output unit 17 that can include a display or other common output means. It is self evident that the data processing of me analytical facility 13 is digital and corresponding converters for converting analogous signals into digital signals are provided.

The system further comprises an input unit 16 by means of which the data or commands can be transmitted to the analytical facility 13. For example, by determining a blood sugar value at the beginning of a night phase from a previously obtained body fluid sample by means of a commercial test strip and corresponding test device and making the blood sugar value available to the analytical facility 13, the analytical facility can estimate the glucose concentration profile during the night phase, in particular in order to indicate whether the level is hazardously below or above the normoglycemic range.

The stability parameters that were determined using the method described above are stored in the data memory 15 in order to be available for a long-term analysis with the scope of diabetes management. The output unit 17 is used to output the therapeutic recommendations derived from the stability parameters to the user of the system. Preferably, these recommendations are also stored in the memory 15. By this means, the system can be used to assess the success of therapeutic recommendations, for example in that stability analysis of sensor data that were recorded in a certain period of time after a recommended therapeutic action is performed.

Thus, embodiments of the analytical method and investigation system are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A system for investigation of the metabolism of a human or animal with regard to a medically significant analyte, comprising:
a sensor for determining measuring data that are correlated with a concentration of a medically significant analyte in a human or animal body fluid, and
an analytical facility for analyzing a series of the measuring data that have been determined by the sensor and are correlated with the concentration of the medically significant analyte in the human or animal body fluid for time points that are distributed over a period of time of at least eight hours, the analytical facility being free from need to obtain a reference value of the medically significant analyte to calibrate the measuring data;
whereby the analytical facility is adapted such that in operation, it selects from the period of time multiple time intervals, which each of the time intervals extend over at least one hour and the analytical facility determines a stability parameter that characterizes the analyte concentration dynamics of change in the time interval for each of the time intervals by analyzing measuring data that are from the time interval, and the analytical facility analyzes the stability parameter and assigns the stability parameter to one of a plurality of predetermined parameter ranges in order to determine disease-related particularities of metabolism.

2. The system as in claim 1 wherein the analytical facility calculates a first derivative over time of the measuring data in a calculation step in order to calculate the stability parameter.

3. The system as in claim 2 wherein the analytical facility calculates a standard deviation of the first derivative over time in a further calculation step.

4. The system as in claim 1 wherein the analytical facility performs a Fourier transformation of a derivative of the measuring data over time to calculate the stability parameter.

5. The system as in claim 1 wherein the analytical facility, performs a linear transformation when operating on the measuring data.

6. The system as in claim 5 wherein the analytical facility selects the linear transformation for each individual time interval such that the mean of the measuring data of a corresponding time interval corresponds to a pre-determined value.

7. The system as in claim 6 wherein the analytical facility selects the linear transformation for each individual time interval such that the standard deviation of the measuring data of the corresponding individual time interval corresponds to a pre-determined value.

8. The system as in claim 1 wherein the analytical facility, is a hand-held device that comprises an output unit, an input unit, and a memory.

9. The system as in claim 1 wherein the analyte is glucose.

10. The system as in claim 9 wherein the analytical facility assigns therapeutic recommendations of a dosage of insulin doses to disease-related particularities of glucose metabolism that have been determined by analysis of the stability parameters.

11. A method for analyzing a series of measuring data, comprising:
- providing a sensor to determine a series of measuring data;
- correlating, using a computer program product, the series of measuring data with a concentration of a medically significant analyte in a human or animal body fluid for time points that are distributed over a period of time of at least 8 hours;
- selecting, using the computer program product, multiple time intervals within the period of time, each time interval extending over at least 1 hour;
- determining, using the computer program product, a stability parameter through a Fourier transformation of a derivative of the measuring data over time, the stability parameter characterizing dynamics of a change of analyte concentration in each time interval by analyzing measuring data that are from that time interval,
- performing, using the computer program product, a linear transformation when operating on the measuring data, the linear transformation being performed individually for each time interval; and
- analyzing, using the computer program product, the stability parameter in order to determine at least one of a diabetic disease and a stage of the diabetic disease, and to further determine a treatment for the diabetic disease.

12. The method as in claim 11 wherein the computer program product can be loaded directly into the memory of a digital computer.

13. A system for investigation of the metabolism of a human or animal with regard to a medically significant analyte, comprising:
- a sensor for determining measuring data that are correlated with a concentration of a medically significant analyte in a human or animal body fluid, and
- means for analyzing a series of measuring data that have been determined by the sensor and are correlated with the concentration of the medically significant analyte in the human or animal body fluid for time points that are distributed over a period of time of at least eight hours by determining a stability parameter that characterizes the analyte concentration dynamics of change and analyzing the stability parameter in order to determine at least one of a diabetic disease, a stage of the diabetic disease, and a treatment for the diabetic disease, wherein the stability parameter is determined through a Fourier transformation of a derivative of the measuring data over time.

14. A method for analyzing a series of measuring data in human body fluid without calibration, comprising:
- sensing a medically significant analyte in a human body to determine measuring data;
- correlating a series of the measuring data with a concentration of a medically significant analyte for time points that are distributed over a period of time of at least 8 hours;
- selecting multiple time intervals each extending over at least a 1 hour the period of time;
- determining a stability parameter characterizing dynamics of the change of analyte concentration in said time interval for each of the time intervals by analyzing measuring data that are from said time interval,
- analyzing the stability parameter free from need to obtain a reference value of the medically significant analyte to calibrate the measuring data; and
- assigning the stability parameter to one of a plurality of predetermined ranges in order to determine disease-related particularities of metabolism.

* * * * *